United States Patent [19]
Leschinsky et al.

[11] Patent Number: 5,873,499
[45] Date of Patent: Feb. 23, 1999

[54] PRESSURE BREAKAWAY DISPENSING GUN

[75] Inventors: Mikhail Leschinsky; Boris Leschinsky, both of Waldwick, N.J.

[73] Assignee: Scientific Resources, Inc., Eatontown, N.J.

[21] Appl. No.: 696,486

[22] Filed: Aug. 14, 1996

[51] Int. Cl.⁶ ............................................. B67D 5/42
[52] U.S. Cl. ........................ 222/327; 222/391; 604/61
[58] Field of Search ................................. 222/326, 327, 222/391, 386, 389, 394; 604/61

[56]  References Cited

U.S. PATENT DOCUMENTS

| | | |
|---|---|---|
| 3,141,583 | 7/1964 | Mapel et al. ........................... 222/327 X |
| 3,493,503 | 2/1970 | Mass . |
| 3,736,932 | 6/1973 | Satchell . |
| 3,757,780 | 9/1973 | Ishikawa . |
| 3,817,389 | 6/1974 | Weichselbaum . |
| 3,859,999 | 1/1975 | Ishikawa . |
| 3,983,513 | 9/1976 | Hargest . |
| 4,127,131 | 11/1978 | Vaillancourt . |
| 4,231,494 | 11/1980 | Greenwood ........................... 222/389 X |
| 4,273,270 | 6/1981 | Kray ........................................... 222/327 |
| 4,339,058 | 7/1982 | Wendt .................................. 222/391 X |
| 4,634,027 | 1/1987 | Kanarvogel ........................... 222/389 X |
| 4,820,276 | 4/1989 | Moreno . |
| 4,834,717 | 5/1989 | Haber et al. . |
| 5,022,563 | 6/1991 | Marchitto et al. . |
| 5,176,657 | 1/1993 | Shields . |
| 5,256,154 | 10/1993 | Liebert et al. . |

*Primary Examiner*—Kevin P. Shaver
*Attorney, Agent, or Firm*—Plevy & Associates

[57] ABSTRACT

A gun for dispensing a fluid from a fluid dispenser has a body portion, a plunger assembly and an advancing mechanism. The body portion has a jaw portion for holding the fluid dispenser in a retained position and adapted for releasing the fluid dispenser when a specific pressure is reached in the chamber of the fluid dispenser. The body portion has a catcher portion for catching the fluid dispenser in a caught position upon being released by the jaw portion. The jaw portion has a pair of legs projecting from the body portion. Each leg has a foot projecting inwardly towards each other and spaced from the body portions, therein defining a flange receiving space. The feet are of such a length to overlie and engage a portion of a flange element of the fluid dispenser. The catcher has a pair of parallel plates; each plate has an opening for receiving the flange of the fluid dispenser in both the retained position and the caught position. The plunger assembly has a plunger rod slideably carried by the body portion. The plunger rod has a plunger element at one end adapted to engage a piston element of the fluid dispenser for moving the piston element towards a nozzle of the fluid dispenser. The advancing mechanism is pivotably carried by the body portion for advancing the plunger assembly in the fluid dispenser towards the nozzle.

20 Claims, 9 Drawing Sheets

continues on next page

PRESSURE BREAKAWAY DISPENSING GUN

FIELD OF THE INVENTION

The invention relates to a dispensing gun for dispensing a liquid carried in a fluid dispenser or syringe and more particularly to a dispensing gun which will decouple the fluid dispenser when a specific high pressure range is reached to relieve the pressure within the fluid dispenser while retaining the fluid dispenser.

BACKGROUND OF THE INVENTION

Various techniques have been used to dispense liquids or semi-solids in a controlled manner. One technique used is a dispensing gun that has a trigger portion which is pulled to move a drive plunger assembly. The drive plunger assembly has a plunger rod with a plunger located at one end. The plunger element is adapted to engage a stopper. The stopper is typically part of a cylindrical tube or carriage which contains the liquid or semi-solid. A dispensing mechanism, such as a nozzle, is located at the other end of the tube from the stopper.

A common style and well known dispensing gun is a caulking gun used to dispense silicone, latex based, oil based, or other style caulk used to seal openings in buildings such as around windows or baths. One of the problem with such guns is that after the operator stops pulling the trigger, the caulk continues to ooze out of the nozzle. In certain operations such continued oozing of the fluid is neither desirable, nor tolerable.

Therefore, dispensing guns were developed which could properly meter the fluid being dispensed. One such dispenser for viscous fluids had the ability to automatically retract the drive plunger element when the trigger was released in order to avoid continued oozing or post extrusion of the viscous fluid. The retraction of the drive plunger allowed the pressure within the cylindrical tube or carriage, also referred to as a fluid dispenser, to be relieved. U.S. Pat. No. 5,022,563 discloses such a dispenser-gun assembly for viscous fluids. However, one concern that has arisen with either style dispensing gun, is that the fluid dispenser either opens or separates from the dispenser-gun because of excess pressure within the fluid dispenser. The excess pressure could be the result of the viscous fluid clogging the nozzle or a filter element, if one exists.

It would be desirable to have a dispenser gun that decouples the fluid dispenser when a specific high pressure range is reached, while still retaining the fluid dispenser to prevent it from dropping to the ground.

SUMMARY OF THE INVENTION

This present invention is directed to a gun for dispensing a fluid from a fluid dispenser. The fluid dispenser is of a type including an elongated tubular barrel member defining a cylindrical chamber, a nozzle element at one end of the barrel member that communicates with the cylindrical chamber, a flange element at the other end of the barrel member, and a piston element that is slidably and sealingly received in the chamber. The piston element is advanceable towards the nozzle for dispensing the fluid through the nozzle. The gun comprises a body portion, a plunger assembly, and an advancing mechanism. The body portion has a releasable retaining mechanism for holding the fluid dispenser in a retained position and adapted for releasing the fluid dispenser when a specific pressure is reached in the chamber of the fluid dispenser. The plunger assembly has a plunger rod slideably carried by the body portion. The plunger rod has a plunger element at one end which is adapted to engage the piston element for moving the piston element towards the nozzle. The advancing mechanism is pivotably carried by the body portion for advancing the plunger assembly in the fluid dispenser towards the nozzle.

In a preferred embodiment the releasable retaining mechanism is a jaw portion adapted to engage a portion of the flange element of the fluid dispenser and adapted to allow the flange element to flex for releasing the fluid dispenser when a specific pressure is reached in the chamber of the fluid dispenser.

In a preferred embodiment, the dispenser gun has a catch for catching the fluid dispenser in a caught position upon being released from the releasing mechanism. The catch is carried by the body portion and has a pair of parallel plates, each plate having an opening for receiving the flange of the fluid dispenser in both the retained position and the caught position.

Further objects, features, and advantages of the present invention will become more apparent to those skilled in the art as the nature of the invention is better understood from the accompanying drawings and detailed descriptions.

BRIEF DESCRIPTION OF THE DRAWINGS

For the purpose of illustrating the invention, there is shown in the drawings forms which are presently preferred; it being understood, however, that this invention is not limited to the precise arrangements and instrumentalities shown.

DETAILED DESCRIPTION OF THE PREFERRED EMBODIMENTS

Referring now to the drawings, wherein like numerals indicate like elements and where prime (' and ") indicate counterparts of such like elements, there is illustrated a side view of a dispenser gun in accordance with the present invention designated generally as 20.

Figure 1:
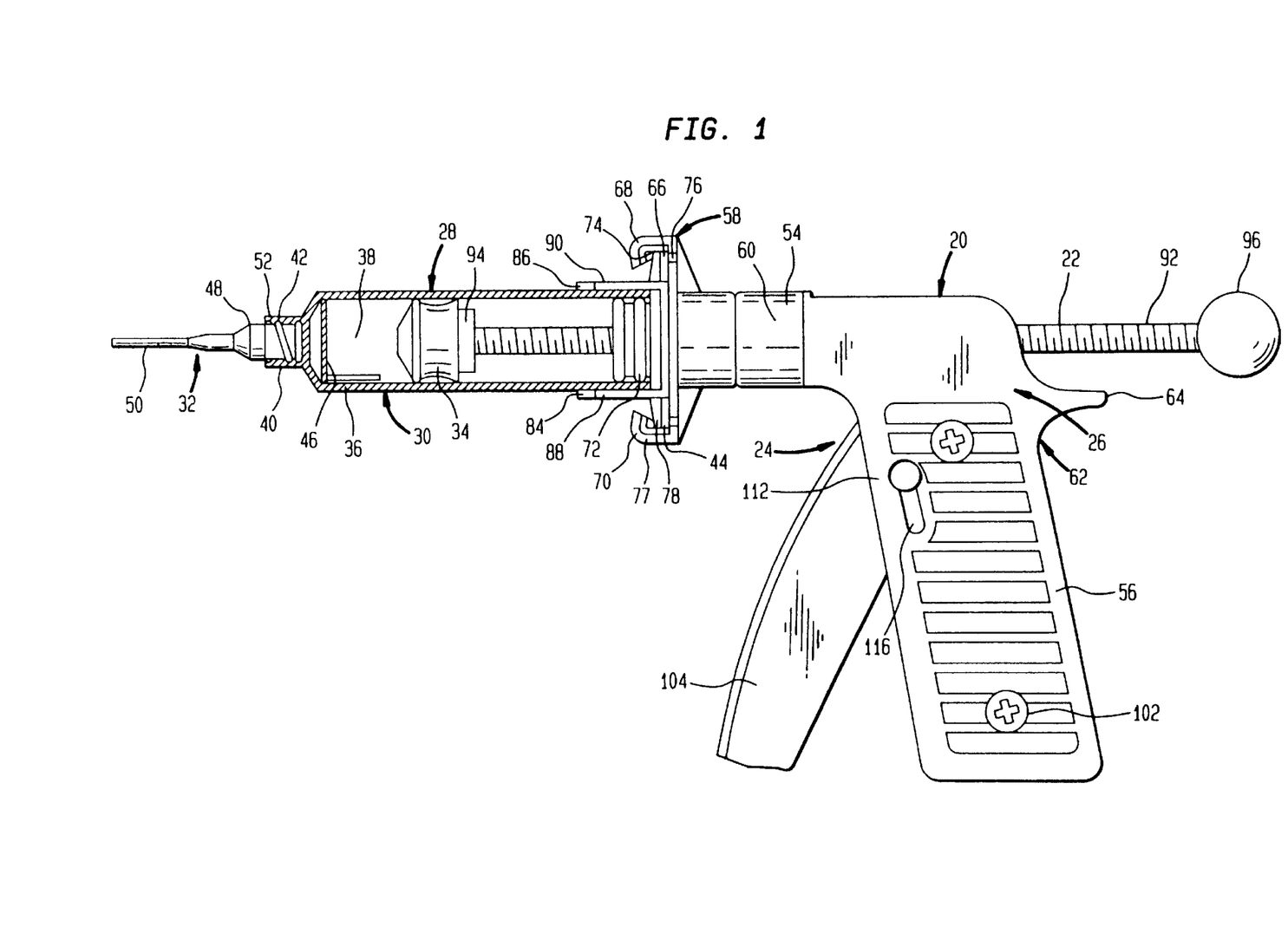
FIG. 1 is a side elevation view of a dispenser gun according to the invention with a fluid dispenser shown in section.

Referring to FIG. 1, the dispenser gun 20 has a drive plunger assembly 22, an advancing mechanism 24, and a body portion 26. The drive plunger assembly 22 and the advancing mechanism 24 are mounted in the body portion 26 so that the advancing mechanism 24 operates for longitudinally advancing and retracting the drive plunger assembly 22. The body portion 26 is adapted for receiving, and retaining and releasing a fluid dispenser 28 when a specific pressure is reached in the fluid dispenser 28 according to the invention.

Figure 2:
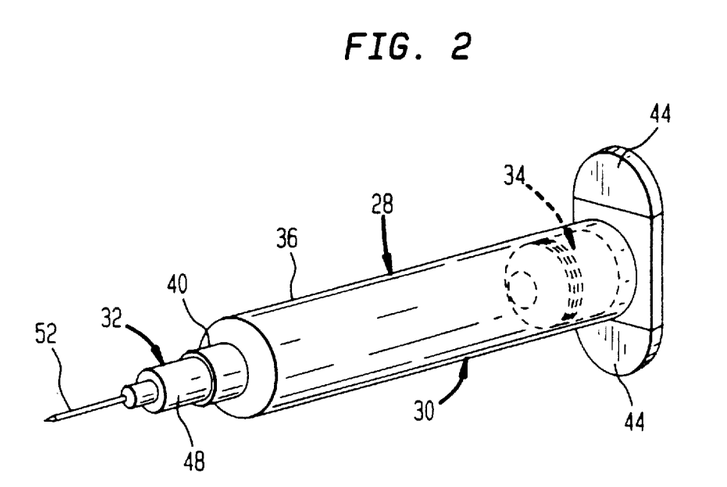
FIG. 2 is a perspective view of the fluid dispenser.

Referring to FIGS. 1 and 2, the fluid dispenser 28 has a barrel member 30, a nozzle element 32, and a piston element 34 which is slideably received in the interior of the barrel member 30. The piston element 34 is advanceable in the barrel member 30 in a direction towards the nozzle element 32 for dispensing a viscous fluid from the barrel member 30 through the nozzle element 32. The barrel member 30 has a cylindrical tubular main portion 36 which defines a cylindrical chamber 38 which receives the piston element 34. The barrel member 30 has a nozzle connection portion 40 which is located at a first end and formed integrally with the cylindrical tubular main portion 36. The nozzle connection portion 40 has female threads 42. The barrel member 30 has a connector flange portion 44 at the opposite second, end of the cylindrical tubular main portion 36. In a preferred embodiment, the fluid dispenser 28 has a filter element 46 located in the cylindrical chamber 38 in proximity to the nozzle connection portion 40. It is also recognized that the filter element 46 may be a stand alone component located in its own housing between the barrel nozzle and the needle.

The nozzle element 32 has a base portion 48 and a tubular dispensing needle portion 50 which extends from the base portion 48. The base portion 48 has male threads 52 adapted to be received by the female threads 42 of the nozzle connection portion 40 of the barrel member 30, such that the tubular dispensing needle 50 is in communication with the chamber 38.

Still referring to FIG. 1, the body portion 26 has a pair of body portion sections 54 and 56, respectively, which are preferably made from a suitable metal and cooperate to define a "pistol grip" type housing, and a fluid dispenser clamp portion 58. The body portion section 54 includes a cylindrical front portion 60 having a reduced aperture (not shown) therethrough for receiving and guiding the drive plunger assembly 22 in its longitudinal movement. The body portion sections 54 and 56 form a handle portion 62 and a rear thumb support 64 which projects rearwardly from the handle portion 62.

The dispenser clamp portion 58 is permanently attached to the cylindrical front portion 60 of one of the body portion sections 54. The dispenser clamp portion 58 is adapted for retaining and releasing the fluid dispenser 28. The clamp portion 58 has a flange portion 66, a pair of jaw portions 68 and 70, and a central portion 72. The central portion 72 of the clamp portion 58 is adapted to be received by the cylindrical chamber 38 of the barrel member 30 so that the fluid dispenser 28 is substantially longitudinally aligned with the drive plunger assembly 22. The jaw portions 68 and 70 each have a foot 74 projecting inwardly towards a central axis "A" defined by the drive plunger assembly 22. Each foot 74 is spaced from the flange portion 66 by a leg portion 76 of the jaw portions 68 and 70. Each of the jaw portions 68 and 70 has a rib 77 on the outer surface which extends over the leg 76 and foot 74 for stiffening. The foot 74 and the flange portion 66 define a flange receiving space 78.

Figure 1A:
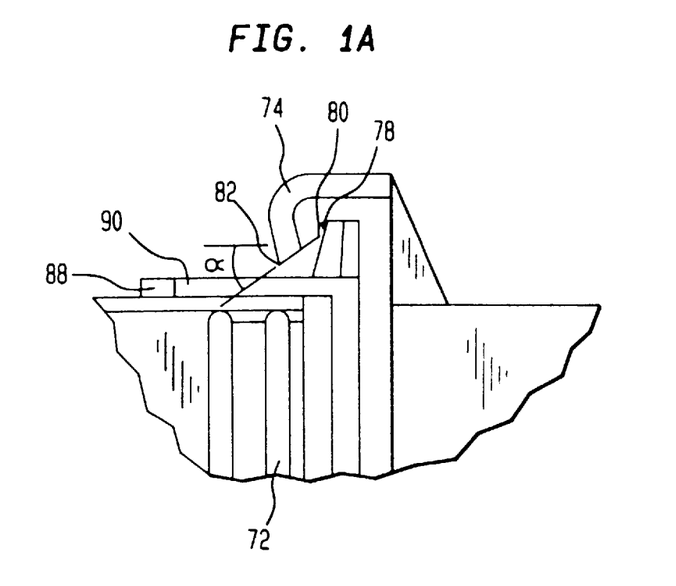
FIG. 1A is an enlarged view of a flange of the fluid dispenser received in a clamp portion of the dispenser gun.

Each foot 74 is tapered such that the edge 80 closer to the body portion 26 and the flange portion 66 is spaced farther from the other foot 74 than the edge 82 farthest from the body portion 26, as best seen in FIG. 1A. In a preferred embodiment, a surface of the foot 74 defined by the edges 80 and 82 forms an angle $\alpha$ of 45 with a line parallel to the central axis "A". While a tapered foot is shown, it is recognized that the flange portion 66 could be designed without the taper.

Still referring to FIG. 1, the dispenser gun 20 has a catching means, generally designated as 84, for catching the fluid dispenser 28. The catching means 84, in a preferred embodiment is a catcher 86 carried by the body portion 26 via the flange portion 66 of the clamp portion 58. The catcher 86 has a pair of generally parallel plate members 88, each member 88 having an opening 90, shown in hidden line in FIG. 1A. Each opening 90 is adapted to receive and retain one of the flanges 44 of the fluid dispenser 28.

The drive plunger assembly 22 of the dispenser gun 20 comprises an elongated cylindrical threaded drive plunger rod 92, which extends along the central axis "A", a drive plunger element 94 on one end of the rod 92, and a ball element 96 on the opposite end of the rod 92. In a preferred embodiment, the rod 92 is a cylindrical threaded rod. It is recognized that other types of rods having notches or grooves can be used. The drive plunger element 94 is of a generally cylindrical configuration and in a preferred embodiment is dimensioned to be received in the interior of the piston element 34.

Figure 3:
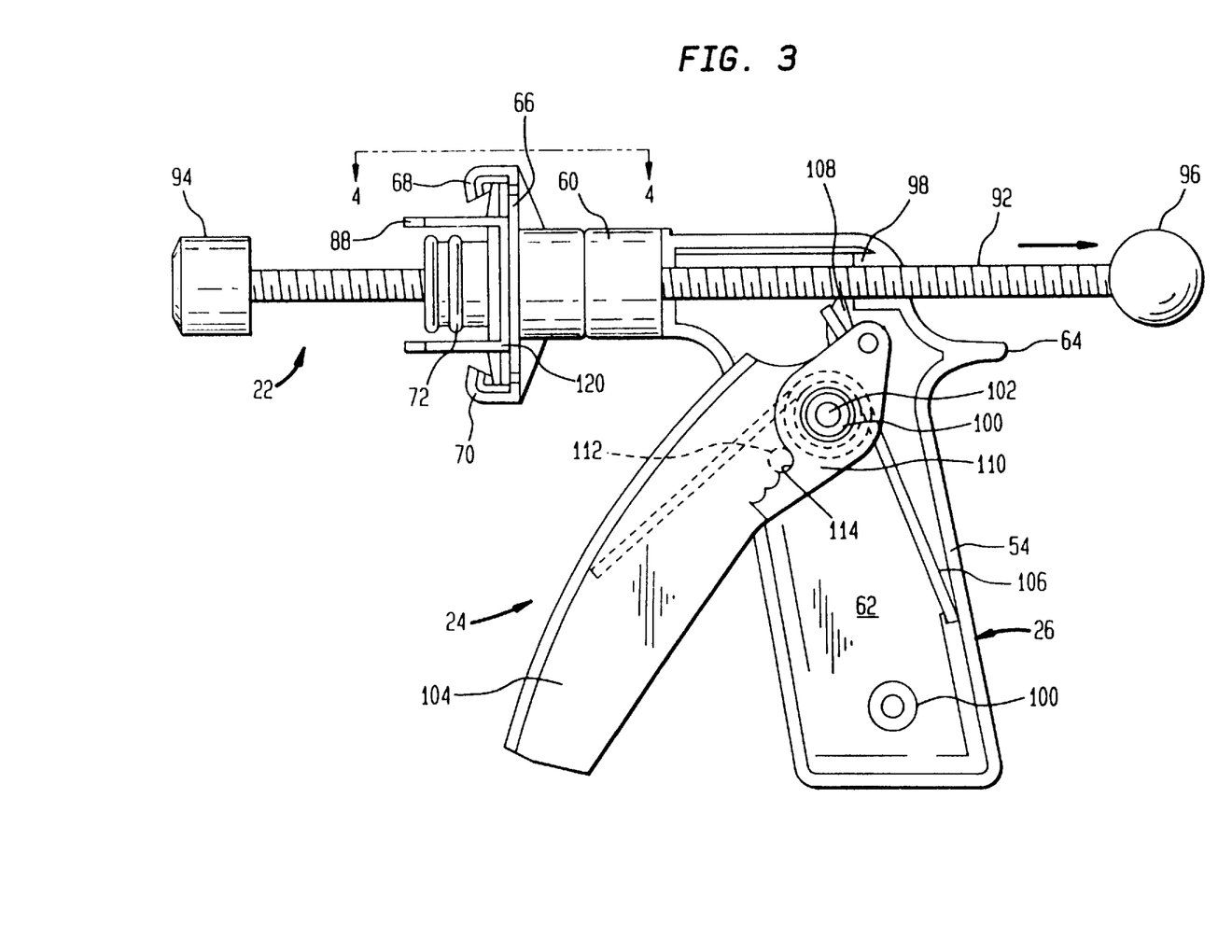
FIG. 3 is a side elevation view of the dispenser gun in a released position with one of the body portion sections removed.

Referring to FIG. 3, the body portion section 56, not shown, is removed from the body portion section 54 to show the interior of the body portion 26. The body portion 26 has a semicircular rear interior boss 98 formed in each of the body portion sections 54 and 56, only body portion 54 is shown, so that when the body portion sections 54 and 56 are assembled together the bosses 98 cooperate to define a reduced aperture for further guiding the drive plunger assembly 22 in its longitudinal movement. A spaced pair of threaded bosses 100 project inwardly into the interior of the handle portion section 62 of the body portion section 54 and the corresponding bosses (not shown) of reduced length project inwardly into the interior of the handle portion section 62 of the body portion section 56. The inwardly projecting tubular bosses 100 in the body portions 54 and 56 are received in a substantially aligned mating engagement in the interior of the body portion 26 and screws 102, as seen in FIG. 1, which are received in threaded engagement in the bosses 100, maintain the body portion sections 54 and 56 in assembled relation.

The advancing assembly 24, as seen in FIG. 3, has a trigger portion 104 which is pivotally mounted on one of the bosses 100, a torsion spring 106 which is received on the same boss 100 so that it engages both the trigger portion 104 and the body portion section 54 for biasing the trigger portion 104 to a forwardly pivoted position, a pawl member 108, an adjustment plate 110 and an adjustment pin 112. The pawl member 108 is pivotally attached to the trigger portion 104 and a torsion spring (not shown) is coaxially mounted with the pawl member 108 on the trigger portion 84 so that it biases the pawl member 108 to an upwardly pivoted position wherein it engages the drive plunger rod 92.

The adjustment plate 110 is integrally formed with the trigger portion 104 and has a series of adjustment notches 114 formed therein. The adjustment pin 112 is slidably received in a slot 116 in the handle portion 62 of the body portion section 56, as seen in FIG. 1, so that it is adjustably positionable in the different notches 114.

Figure 4:
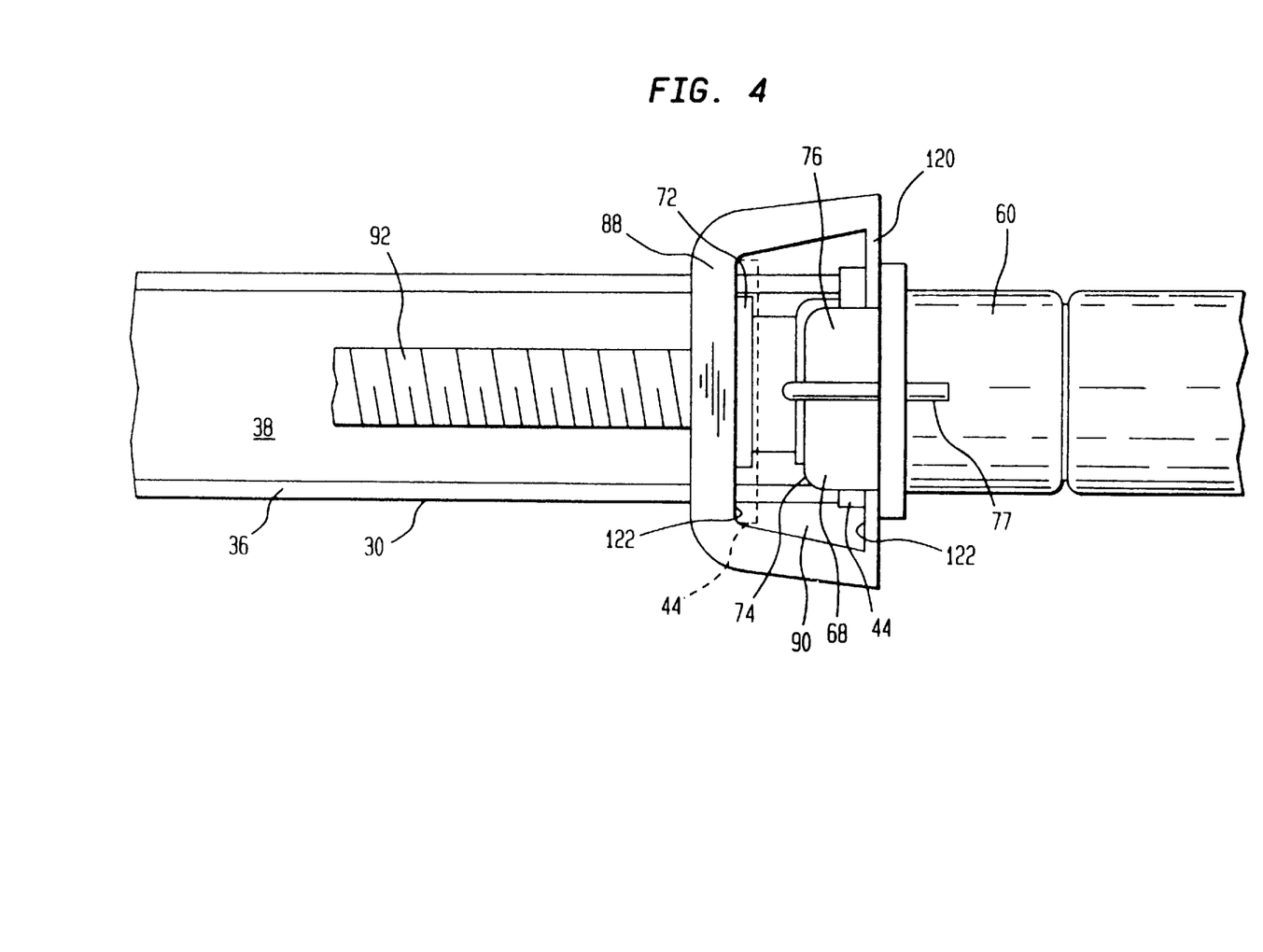
FIG. 4 is a top view of the dispenser gun taken along line 4—4 in FIG. 3, with the fluid dispenser shown in section.

FIG. 4 shows the top view taken of the dispenser gun 20 including the opening 90 of the plate member 88. The catcher 86 has a base 120 mounted to the flange portion 66 of the clamp portion. Each of the plate members 88, only one seen, are generally "D" shaped and project from the base 120. The opening 90 has a pair of generally parallel edges 122 for engaging the flange portion 44 in the retained position and the caught position, respectively. The central portion 72 of the clamp portion 58 is seen through the barrel member 30 of the fluid dispenser 28. The flange 44 of the fluid dispenser 28 is shown in phantom in the caught position. The rib 77 of the jaw portion 68 is seen centered on the foot 74 and leg portion 76.

Accordingly, for use and operation of the dispenser gun 20, the adjustment pin 112 is moved to the uppermost notch 114, as seen in FIG. 1. With the adjustment pin 112 in the uppermost notch 114, the trigger portion 104 is normally maintained in a fully forwardly pivoted position wherein the pawl member 108 engages the boss 98 to disengage the pawl member 108 from the rod 92 as illustrated in FIG. 3. The drive plunger assembly 22 is moved rearwardly to a fully retracted position.

The fluid dispenser 28 is then mounted on the dispenser gun 20 as shown in FIG. 1. This is achieved by the drive plunger element 94 being placed in the cylindrical chamber 38. The central portion 72 of the clamp positioned in the open end portion of the barrel member 30 so on anges 44 of the fluid dispenser 28 are positioned between the jaw portions 68 and 70. The fluid dispenser 28 is rotated, urging the flanges 44 and the adjacent end portions of the barrel member 30 into engagement with the flange portion 66 of the dispenser clamp portion 58. The fluid dispenser 28 is in the retained position.

Figure 5:
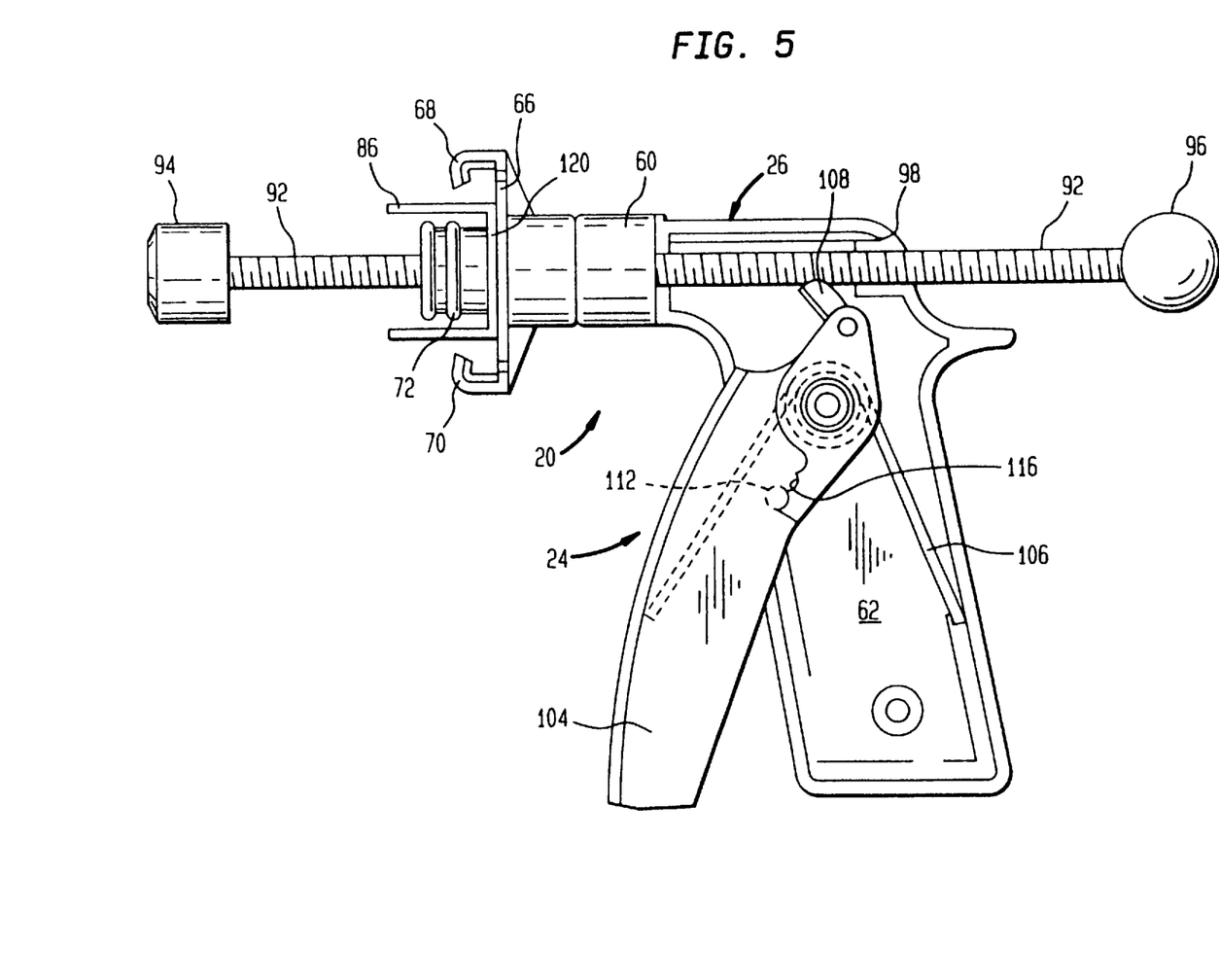
FIG. 5 is a side elevation view of the dispenser gun in a retracted position with one of the body portion sections removed.

Referring to FIG. 5, the adjustment pin 112 can then be repositioned in one of the other notches 114, seen in FIG. 1. The repositioning of the adjustment pin 112 into one of the lower two notches 114 adjust the stroke of the piston. The drive plunger assembly 22 is manually advanced in a forward direction with respect to the body portion 26 by urging the ball element 98 forward until the drive plunger element 94 is received in engagement with the piston element 34, seen in FIG. 1. The drive plunger assembly 22 can move forward but in the rearward direction, because of the forwardly angled pawl member 108 allows ratcheting only in one direction.

Figure 6:
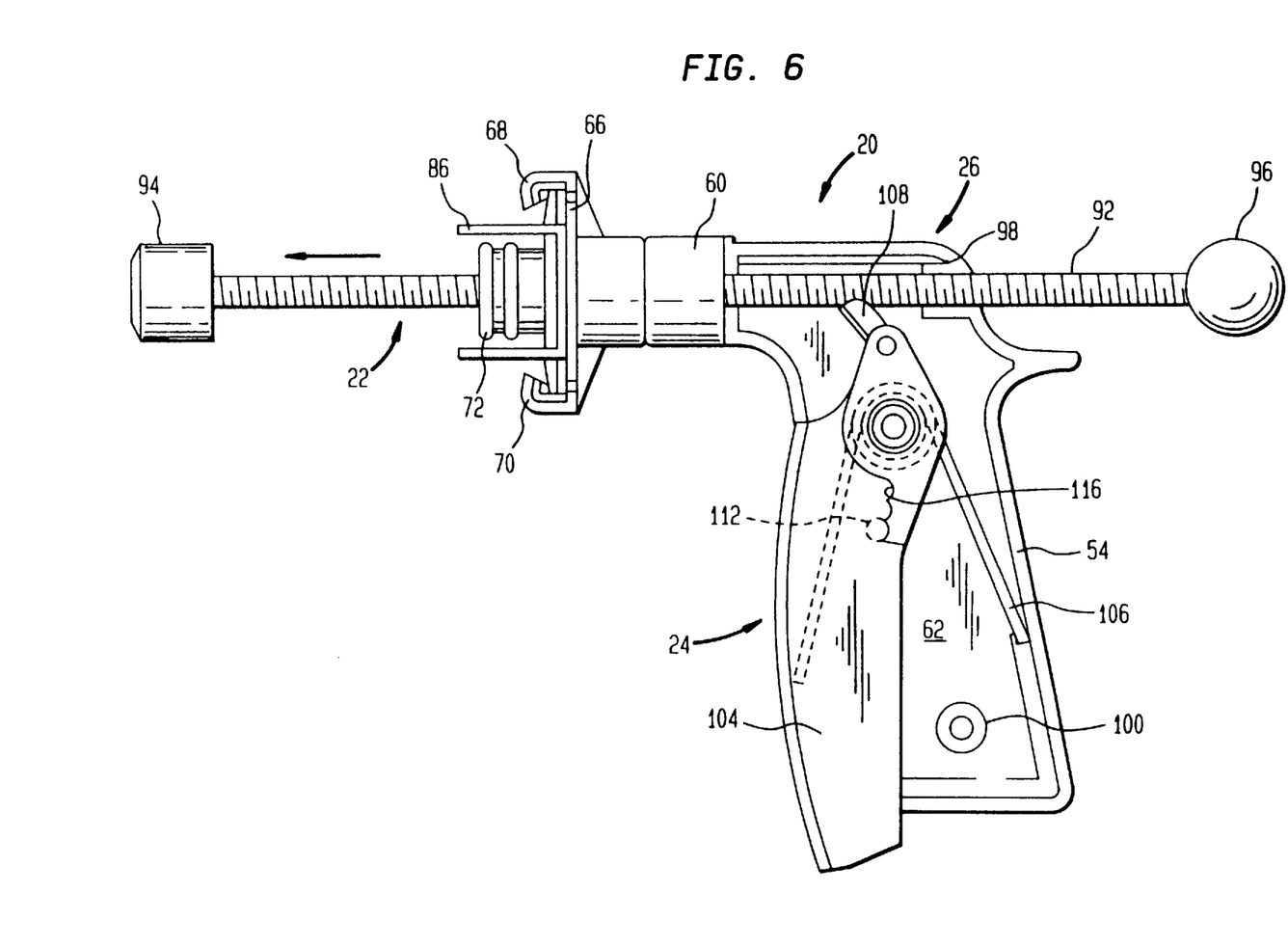
FIG. 6 is a side elevation view of the dispenser gun in an advanced position with one of the body portion sections removed.

When the trigger portion 104 is squeezed or drawn rearwardly toward the handle portion 62, the pawl member 108 advances the drive plunger assembly 22 forward as illustrated in FIG. 6. When pawl member 108 advances the drive plunger element 94 forward, the piston element 34 is also advanced in the chamber 38, as seen in FIG. 1, so that a fluid contained in the chamber 38 is dispensed through the dispensing needle 50.

The pawl member 108 is not constantly engaged with the rod 92, and ratchets back to engage the piston rod 92 in a new position to advance the piston with every new stroke. The advancing mechanism 24 has another pawl member, not shown, to stop the rod 92 from moving back when the trigger is released. When the trigger portion 104 is squeezed or drawn rearwardly toward the handle portion 62, the drive plunger assembly 22 is advanced longitudinally forward from a first position to a second, further advanced position. The other pawl, not shown, stops the rod 92 from moving back.

Once a desired quantity of fluid has been dispensed from the chamber 38, the trigger portion 104 is released and is biased back to its original forward pivoted position by the torsion spring 106. As the trigger portion 104 is returned to its original forward pivoted position, the drive plunger assembly 22 is moved rearwardly to its original retracted position by the pawl member 108. The drive plunger element 94 is normally either fully or partially disengaged from the piston element 34 so that the external pressure applied to the piston element 34 by the drive plunger element 94 is released. Since the piston element 34 can freely slide in a rearward direction in the barrel member 30, the piston element 34 is normally moved rearwardly in the barrel member 30 by the expansion of the fluid in the chamber 38 to relieve the internal pressure on the fluid. As a result, post extrusion of fluid from the chamber 38 through the dispensing needle 50 is effectively eliminated so that the amount of fluid dispensed from the chamber 38 can be precisely controlled by appropriately manipulating the dispenser gun 20.

Referring to FIGS. 1 and 1A, if the tubular dispensing needle portion 50 or the filter element 46 located in the cylindrical chamber 38 clogs or for some other reason the pressure builds up in the chamber 38, typically when the trigger portion 104 is being squeezed or drawn rearwardly, the flanges 44 of the fluid dispenser 28 flex slightly to release the fluid dispenser 28 from the dispenser clamp portion 58.

Upon releasing the fluid dispenser 28 by the clamp portion 58, the fluid dispenser 28 is retained by the catcher 86 in a caught position, with the flange portions 44 retained in the openings 90 of the members 88. The fluid dispenser 28 has moved enough to reduce the pressure within the chamber 38, however the piston element 34 is still retained in the chamber 38 to prevent fluid from being lost out the open end of the chamber 38, the flange portions 44.

In a preferred embodiment for a 10 cc fluid dispenser 28, where it is desired to maintain the internal pressure within the chamber below 90 psi, the distance between the inner edges 80 of the jaw portions 68 and 70 is in a range of 1.150 to 1.155 inches. The 10 cc fluid dispenser 28 has a cylindrical tubular main portion 36 that has an outside diameter of 0.740" and an inner diameter of approximately 0.625 inches. The flange 44 has an overall distance of 1.340".

Figure 7:
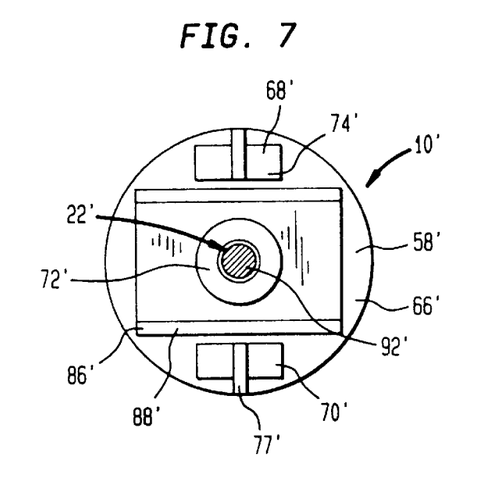
FIG. 7 is a front section view of the dispenser gun showing an alternative of a dispenser clamp portion.

Referring to FIG. 7, a front sectional view of the dispenser gun 10' shows an alternative embodiment of a dispenser clamp portion 58'. The dispenser clamp portion 58' is adapted for retaining and releasing the fluid dispenser 28, not shown. The clamp portion 58' has a flange portion 66', a pair of jaw portions 68' and 70', and a central portion 72'. The central portion 72' of the clamp portion 58' is adapted to be received by the cylindrical chamber 38 of the barrel member 30 so that the fluid dispenser 28 is substantially longitudinally aligned with the drive plunger assembly 22'. The jaw portions 68' and 70' each have a foot 74' projecting inwardly towards the central axis "A", which is projecting out of the page in FIG. 7. (The elongated cylindrical threaded drive plunger rod 92', shown in section, extends along the central axis "A".)

In contrast to the first embodiment, the feet 74' do not project towards the central axis "A" an equal amount. The foot 74' of the jaw portion 68' extends further towards the central axis "A" than the foot 74' of the jaw portion 70'. The total distance between the feet 74' is similar to that in the first embodiment, only the relative position of the central axis in that space has been shifted.

Similar to the first embodiment, each foot 74' is spaced from the flange portion 66' by a leg portion, not seen, of the jaw portions 68' and 70'. Each of the jaw portions 68' and 70' has a rib 77' on the outer surface which extends over the leg and foot 74' for stiffening.

This embodiment works in a manner similar to the first embodiment with the exception that one of the jaw portions 70' releases the flange 44 of the fluid dispenser 28 first and then the other jaw portion 68' releases the other flange 44'.

The dispenser gun 10 has a catching means, a catcher 86', carried by the body portion, not seen, via the flange portion 66' of the clamp portion 58'. This is similar to the first embodiment. The catcher 86' has a pair of generally parallel plate members 88' which are equally spaced from the central axis "A".

Figure 8:
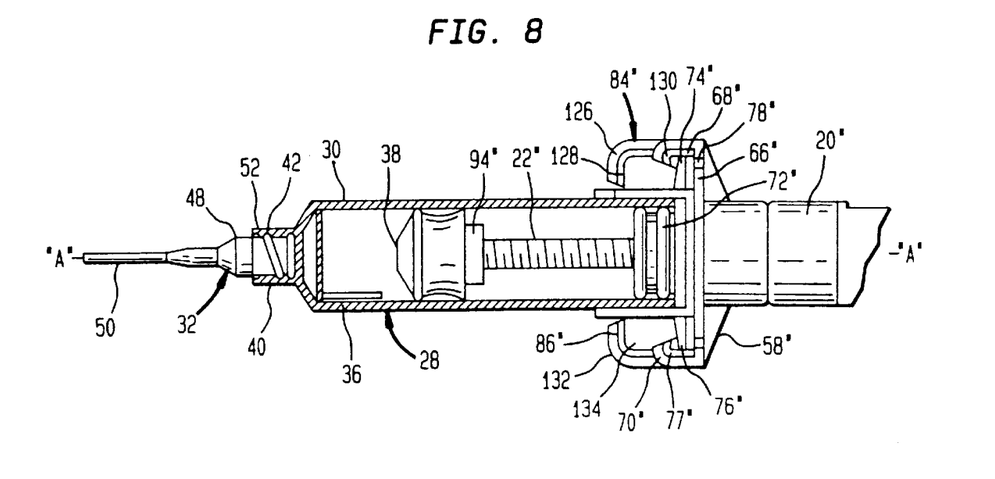
FIG. 8 is a side elevation view of a forward portion of an alternative embodiment of the dispenser gun. The fluid dispenser in section is shown carried by the dispenser gun.

An alternative embodiment of a catching means 84" is shown in FIG. 8. Similar to FIG. 1, the dispenser gun 20" has a dispenser clamp portion 58" adapted for retaining and releasing the fluid dispenser 28". The clamp portion 58" has a flange portion 66", a pair of jaw portions 68", and 70", and a central portion 72". The central portion 72" of the clamp portion 58" is adapted to be received by a cylindrical chamber 38" of a barrel member 30" so that the fluid dispenser 28" is substantially longitudinally aligned with a drive plunger assembly 22" of the dispenser gun 20". The jaw portions 68" and 70" each have a foot 74" projecting inwardly towards a central axis "A" defined by the drive plunger assembly 22". Each of the feet 74" is spaced from the flange portion 66" by a leg portion 76" of the jaw portions 68" and 70". Each of the jaw portions 68" and 70" has a rib 77" on the outer surface which extends over the leg 76" and foot 74" for stiffening. The foot 74' and the flange portion 66" define a flange receiving space 78".

Still referring to FIG. 8, the dispenser gun 20" has a catching portion 86" for the catching means 84". The catching portion 86" has a second set of jaw portions 126 which project outward from the first jaw portions 68 and 70. Each of the second set of jaw portions 126 has a foot 128 projecting inwardly towards a central axis "A" defined by the drive plunger assembly 22". The feet 128 of the catching portion 86" extend further towards the centerline "A", such that they typically contact the outer surface of the cylindrical tubular main portion 36 of the fluid dispenser 28. Each foot 128 is spaced from the first flange portion 66" by a leg portion 130 of the jaw portions 126. Each of the jaw portions 126 has a rib 132 on the outer surface which extends over the leg 130 and foot 128 for stiffening. The foot 128 of the jaw portion 126 and the foot 74" of the dispenser clamp portion 58" and the flange portion 66 define a second flange receiving space 134.

When the flanges 44" of the fluid dispenser 28 flex therein being released by the jaw portions 68" and 70" of the dispenser clamp portion 58", the flanges 44" flex initially and then return towards their normal positions. This return to the normal position in combination with the feet 128 of the catching portion 86" being longer, results in the feet 128 of the second set of jaws 126 catching the fluid dispenser 28. Similar to the first embodiment, the fluid dispenser 28 has moved enough to reduce the pressure within the chamber 38, however the piston element 34" is still retained in the chamber 38 to prevent fluid from being lost out the open end of the chamber 38, the end of the flange portions 44.

Figure 9:
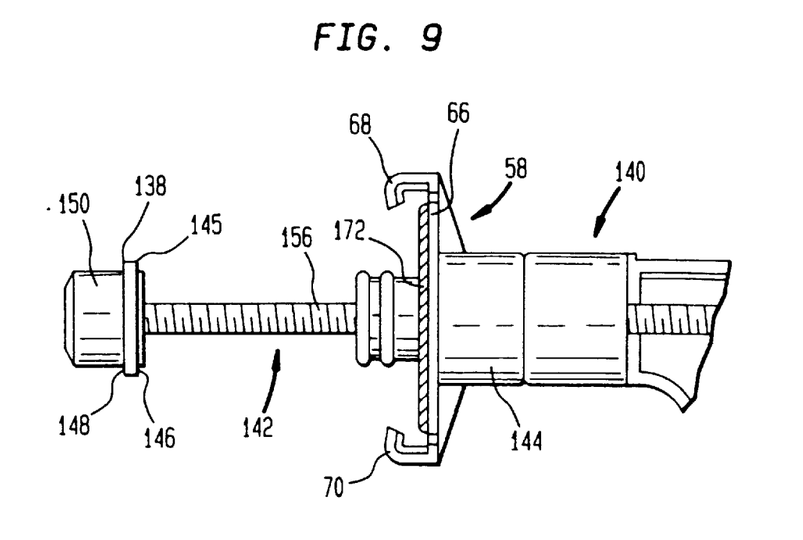
FIG. 9 is a side elevation view of a forward portion of a dispenser gun of showing an alternative embodiment.
Figure 12:
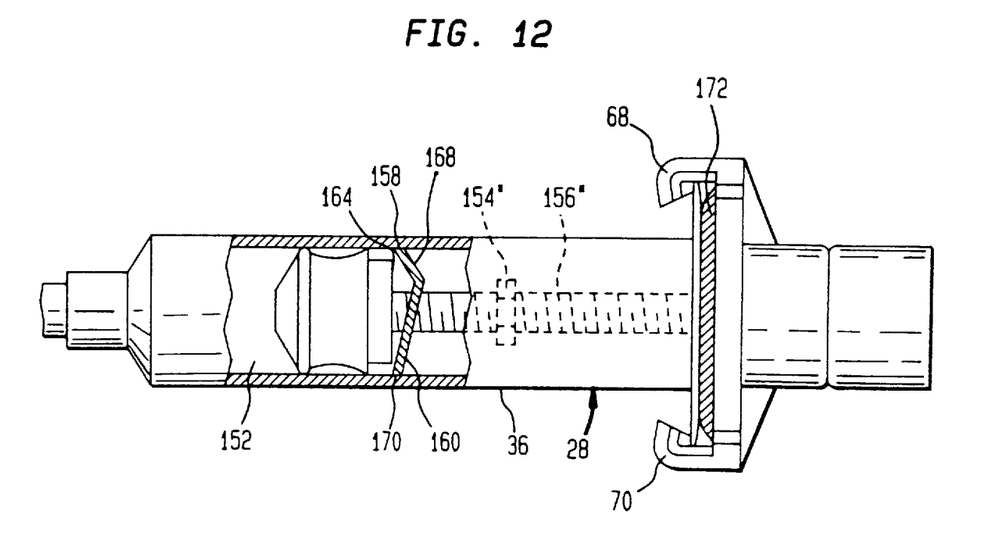
FIG. 12 is an enlarged side elevation view of the alternative embodiment shown in FIG. 11 of the dispenser gun. A portion of the fluid dispenser is shown in section.

FIG. 9 shows an alternative embodiment of a catching means 138 for a dispenser gun 140. In contrast to the previous embodiments, the catching means 138 is carried by a drive plunger assembly 142 of the dispenser gun 140, not the body portion 144. The catching means 138 is a friction element 145, such as an O-ring 146, carried in a groove 148 on a drive plunger element 150 of the drive plunger assembly 142. The O-ring 146 engages an inner surface 152, as seen in FIG. 12, of the cylindrical tubular main portion 36 of the fluid dispenser 28.

Upon release of the fluid dispenser 28 by the dispenser clamp portion, the interference and friction created between the O-ring 146 and the inner surface 152 of the cylindrical tubular main portion 36 of the fluid dispenser 28, limits the movement of the fluid dispenser 28 relative to the drive plunger assembly 142 of the dispenser gun 140. The fluid dispenser 28 has moved enough to reduce the pressure within the chamber 38, however the piston element 34 is still retained in the chamber 38 to prevent fluid from being lost out the open end of the chamber 38, the end of the flange portions 44.

Figure 10:
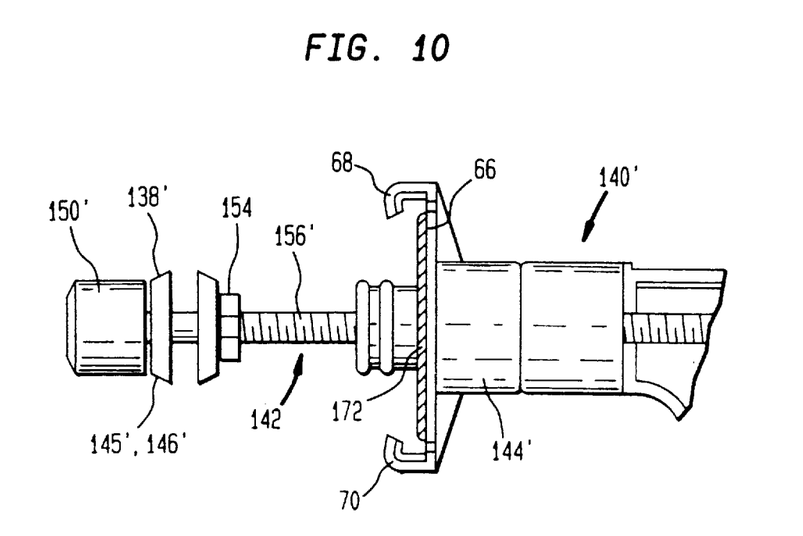
FIG. 10 is a side elevation view of a forward portion of a dispenser gun of an alternative embodiment.

An alternative embodiment of a catching means 138' for a dispenser gun 140 is shown in FIG. 10. Similar to the previous embodiment, the catching means 138' is carried by a drive plunger assembly 142' of the dispenser gun 140, not the body portion 144. The catching means 138' is a friction element 145', like the last embodiment, but is a separate resilient washer 146' carried behind a drive plunger element 150', rather than an O-ring 146 carried by the drive plunger element. The washer 146' in a preferred embodiment has a pair of annular portions. A threaded fastener 154 is received by the threaded drive plunger rod 156' to assist in positioning the frictional engaging washer 146'. The washer 146' engages the inner surface 152 of the cylindrical tubular main portion 36 of the fluid dispenser 28.

Upon release of the fluid dispenser 28 by the dispenser clamp portion, the interference and friction created between the washer 146' and the inner surface 152 of the cylindrical tubular main portion 36 of the fluid dispenser 28, limits the movement of the fluid dispenser 28 relative to the drive plunger assembly 142' of the dispenser gun 140. The fluid dispenser 28 has moved enough to reduce the pressure within the chamber 38, however the piston element 34 is still retained in the chamber 38 to prevent fluid from being lost out the open end of the chamber 38.

Figure 11:
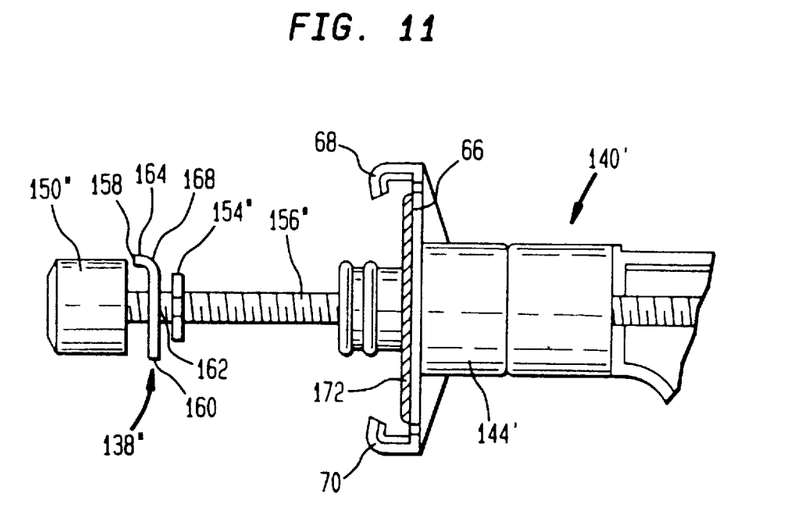
FIG. 11 is a side elevation view of a forward portion of a dispenser gun of an alternative embodiment.

Referring to FIGS. 11 and 12, the dispenser gun 140 has another alternative embodiment of a catching means 138". The catching means 138" is a pivotal catch plate 158 pivotably mounted on the drive plunger rod 156". A threaded fastener 154" is received by the threaded drive plunger rod 156" to assist in positioning the catch plate 158. The catch plate 158 has a large plate portion 160 having a hole 162 through which the drive plunger rod 156" extends, and a smaller plate portion 164 which projects from the larger plate portion 160 at an angle. In a preferred embodiment, the range of the angle is between 90 degrees and 140 degrees. The plate portions 160 and 164 are integral.

The smaller plate 164 has an outside surface 168 which is typically parallel and in close proximity to the inner surface 152 of the cylindrical tubular main portion 36 and the larger plate 160 has an edge 170 which is likewise in close proximity to the inner surface 152. Upon release of the fluid dispenser 28 by the dispenser clamp portion, the movement of the fluid dispenser 28 relative to the catch plate 158 causes the plate 158 to rotate and engage the inner surface 152 of the main portion 36 of the fluid dispenser 28, therein limiting the movement of the fluid dispenser 28 relative to the drive plunger assembly 142 of the dispenser gun 140. The fluid dispenser 28 has moved enough to reduce the pressure within the chamber 38, however the piston element 34 is still retained in the chamber 38 to prevent fluid from being lost out the open end.

FIGS. 9–12 show a washer 172 which may be required to properly seat the flange 44 of the fluid dispenser 28 in the dispenser clamp portion 60 of the dispenser gun. It is recognized that one of the catching means shown in FIGS. 9–12 could be used in conjunction with one of the catching means shown in FIG. 1–8. For example, the O-ring 146 shown in FIG. 9 could be used in conjunction with the catcher 86 of FIGS. 1–6.

The present invention may be embodied in other specific forms without departing from the spirit or essential attributes therefore and, accordingly, references should be made to appended claims, rather than to the foregoing specification, as indicating the scope of the invention.

We claim:

1. A gun for dispensing a fluid from a fluid dispenser including an elongated tubular barrel member defining a cylindrical chamber, a nozzle element at one end of the barrel member and communicating with the cylindrical chamber, a flange element at the other end of the barrel member, and a piston element slidably and sealingly received in the chamber, the piston element being advanceable towards the nozzle for dispensing the fluid through the nozzle, the gun comprising:

a body portion having a releasable retaining means for holding the fluid dispenser in a retained position and for releasing the fluid dispenser when a specific pressure is reached in the chamber of the fluid dispenser;

a plunger assembly having a plunger rod slideably carried by the body portion, the plunger rod having a plunger element at one end, the plunger element adapted to engage the piston element for moving the piston element towards the nozzle;

an advancing mechanism pivotably carried by the body portion for advancing the plunger assembly in the fluid dispenser towards the nozzle; and a catching means for catching the fluid dispenser in a caught position upon being released from the releasable retaining means.

2. A gun for dispensing a fluid from a fluid dispenser as in claim 1 wherein the catching means is a frictional element carried by the plunger assembly and adapted to be received in the cylindrical chamber of the fluid dispenser.

3. A gun for dispensing a fluid from a fluid dispenser as in claim 1 wherein the catching means is an "L" shaped plate pivotally carried by the plunger assembly and adapted to be received in the cylindrical chamber of the fluid dispenser.

4. A gun for dispensing a fluid from a fluid dispenser as in claim 1 wherein the catching means is carried by the body portion.

5. A gun for dispensing a fluid from a fluid dispenser as in claim 4 wherein the catching means is a catcher having a pair of parallel plates, each plate having an opening for receiving the flange of the fluid dispenser in both the retained position and the caught position.

6. A gun for dispensing a fluid from a fluid dispenser as in claim 4 wherein the releasable retaining means is a jaw portion adapted to engage a portion of the flange element and adapted to allow the flange element to flex for releasing the fluid dispenser when a specific pressure is reached in the chamber of the fluid dispenser and the catching means is a second jaw portion spaced from the first jaw portion such that the first jaw portion is interposed between the second jaw portion and the body portion.

7. A gun for dispensing a fluid from a fluid dispenser including an elongated tubular barrel member defining a cylindrical chamber, a nozzle element at one end of the barrel member and communicating with the cylindrical chamber, a flange element at the other end of the barrel member, and a piston element slidably and sealingly received in the chamber, the piston element being advanceable towards the nozzle for dispensing the fluid through the nozzle, the gun comprising:

a body portion having a releasable retaining means for holding the fluid dispenser in a retained position and for releasing the fluid dispenser when a specific pressure is reached in the chamber of the fluid dispenser;

a plunger assembly having a plunger rod slideably carried by the body portion and defining a centerline about which the plunger rod extends, the plunger rod having a plunger element at one end, the plunger element adapted to engage the piston element for moving the piston element towards the nozzle; and an advancing mechanism pivotably carried by the body portion for advancing the plunger assembly in the fluid dispenser towards the nozzle, wherein the releasable retaining means is a jaw portion having a pair of legs projecting from the body portion, each leg having a foot projecting inwardly towards each other and spaced from the body portion, therein defining a flange receiving space, one of the feet extending further towards the centerline than the other foot, the feet being of such length to overlie and engage a portion of the flange element of the fluid dispenser and to allow the flange element to flex for releasing the fluid dispenser when a specific pressure is reached in the chamber of the fluid dispenser.

8. A gun for dispensing a fluid from a fluid dispenser as in claim 7 wherein the foot is tapered such that the tapered edge closer to the body portion and flange portion is spaced farther from the other foot than the tapered edge farthest from the body portion and flange portion.

9. A gun for dispensing a fluid from a fluid dispenser including an elongated tubular barrel member defining a cylindrical chamber; a nozzle element at one end of the barrel member and communicating with the cylindrical chamber; a flange element at the other end of the barrel member; and a piston element slidably and sealingly received in the chamber, the piston element being advanceable towards the nozzle for dispensing the fluid through the nozzle, the gun comprising:

a body portion, the body portion having a retaining means for holding the fluid dispenser;

a plunger assembly having a plunger rod slideably carried by the body portion, the plunger rod having a plunger element at one end, the plunger element adapted to engage the piston element for moving the piston element towards the nozzle;

an advancing mechanism pivotably carried by the body portion for advancing the plunger assembly in the fluid dispenser towards the nozzle; and a catch means for catching the fluid dispenser in a caught position upon release.

10. A gun for dispensing a fluid from a fluid dispenser as in claim 9, wherein the retaining means for holding the fluid dispenser is a jaw portion having a pair of legs projecting from the body portion and each leg having a foot projecting inwardly towards each other and spaced from the body portions, therein defining a flange receiving space, the feet of such a length to overlie and engage a portion of the flange element and adapted to allow the flange element to flex for releasing the fluid dispenser when a specific pressure is reached in the chamber of the fluid dispenser.

11. A gun for dispensing a fluid from a fluid dispenser as in claim 9 wherein the catching means is carried by the body portion.

12. A gun for dispensing a fluid from a fluid dispenser as in claim 11 wherein the catching means is a catcher having a pair of parallel plates, each plate having an opening for receiving the flange of the fluid dispenser in both a retained position and the caught position.

13. A gun for dispensing a fluid from a fluid dispenser as in claim 4 wherein the retaining means is a jaw portion adapted to engage a portion of the flange element and adapted to allow the flange element to flex for releasing the fluid dispenser when a specific pressure is reached in the chamber of the fluid dispenser and the catching means is a second jaw portion spaced from the first jaw portion such that the first jaw portion is interposed between the second jaw portion and the body portion.

14. A gun for dispensing a fluid from a fluid dispenser including an elongated tubular barrel member defining a cylindrical chamber; a nozzle element at one end of the barrel member and communicating with the cylindrical chamber; a flange element at the other end of the barrel member; a piston element slidably and sealingly received in the chamber, the piston element being advanceable towards the nozzle for dispensing the fluid through the nozzle, the gun comprising:

a body portion having a jaw portion for holding the fluid dispenser in a retained position and adapted for releasing the fluid dispenser when a specific pressure is reached in the chamber of the fluid dispenser, and a catcher portion for catching the fluid dispenser in a caught position upon being released by the jaw portion, the jaw portion having a pair of legs projecting from the body portion and each leg having a foot projecting inwardly towards each other and spaced from the body portions, therein defining a flange receiving space, the feet of such a length to overlie and engage a portion of the flange element, the feet being tapered such that an edge closer to the body portion is spaced further from the other foot than an edge further to body portion, the catcher having a pair of parallel plates, each plate having an opening for receiving the flange of the fluid dispenser in both the retained position and the caught position;

a plunger assembly having a plunger rod slideably carried by the body portion, the plunger rod having a plunger element at one end, the plunger element adapted to engage the piston element for moving the piston element towards the nozzle; and an advancing mechanism pivotably carried by the body portion for advancing the plunger assembly in the fluid dispenser towards the nozzle.

15. A gun for dispensing a fluid from a fluid dispenser as in claim 14 wherein the plunger rod defines a centerline about which the plunger rod extends and each of the feet project equally toward the centerline.

16. A gun for dispensing a fluid from a fluid dispenser as in claim 14 wherein the plunger rod defines a centerline about which the plunger rod extends and one of the feet extends further towards the centerline than the other foot.

17. A gun for dispensing a fluid from a fluid dispenser as in claim 14 wherein the jaw portions have an angle of range of 30 degrees to 60 degrees.

18. A gun for dispensing a fluid from a fluid dispenser as in claim 14 wherein the jaw portions are spaced by greater than 90 percent of the distance of the flange.

19. A gun for dispensing a fluid from a fluid dispenser as in claim 14 wherein the jaw portions are spaced apart a distance of between 1.150 to 1.155 inches for use with a fluid dispenser having a flange of 1.340 inches nominal distance.

20. A dispenser-gun assembly for dispensing a fluid comprising:

a) a dispenser portion including:
  i) an elongated tubular member having an elongated cylindrical chamber therein for containing the fluid, the chamber having a first end and an opposite second end;
  ii) a nozzle integral to the tubular member and communicating with the first end of the chamber for receiving the fluid therefrom and for dispensing the fluid;
  iii) a flange element at the second end of the tubular member;
  iv) a piston element slideably and sealingly received in the chamber, the piston being advanceable towards the nozzle for dispensing the fluid through the nozzle; and
  v) a filter element carried in the elongated cylindrical chamber in proximity to the nozzle for filtering the fluid; and b) a gun portion including:
  i) a body portion, the body portion having a jaw portion for receiving the flange element of the fluid dispenser in a retained position and adapted for releasing the fluid dispenser when a specific pressure is reached in the chamber of the fluid dispenser;
  ii) a plunger assembly having a plunger rod slidebly carried by the body portion, the plunger rod having a plunger element at one end, the plunger element adapted to engage the plunger element for moving the plunger element towards the nozzle;
  iii) an advancing mechanism pivotably carried by the body portion for advancing the plunger assembly in the fluid dispenser towards the nozzle; and
  iv) a catcher for catching the fluid dispenser in a caught position upon being released from the releasable releasing means, the catcher carried by the body portion and having a pair of parallel plates, each plate having an opening for receiving the flange of the fluid dispenser in both the retained position and the caught position.

* * * * *